US011433189B2

(12) United States Patent
Power

(10) Patent No.: US 11,433,189 B2
(45) Date of Patent: Sep. 6, 2022

(54) AEROSOL DELIVERY SYSTEM WITH HUMIDIFICATION

(71) Applicant: Stamford Devices Limited, Galway (IE)

(72) Inventor: Patrick Power, Galway (IE)

(73) Assignee: Stamford Devices Limited, Galway (IE)

( * ) Notice: Subject to any disclaimer, the term of this patent is extended or adjusted under 35 U.S.C. 154(b) by 206 days.

(21) Appl. No.: 16/853,039

(22) Filed: Apr. 20, 2020

(65) Prior Publication Data

US 2020/0316319 A1 Oct. 8, 2020

Related U.S. Application Data

(63) Continuation of application No. 15/300,513, filed as application No. PCT/EP2015/062972 on Jun. 10, 2015, now Pat. No. 10,661,031.

(30) Foreign Application Priority Data

Jun. 10, 2014 (EP) .................................... 14171765

(51) Int. Cl.
*A61M 11/02* (2006.01)
*A61M 11/00* (2006.01)
(Continued)

(52) U.S. Cl.
CPC ............. *A61M 11/02* (2013.01); *A61M 11/00* (2013.01); *A61M 11/06* (2013.01);
(Continued)

(58) Field of Classification Search
CPC ................ A61M 16/00; A61M 16/024; A61M 16/1045; A61M 16/1075–1095; A61M 16/16; A61M 16/161; A61M 11/00; A61M 11/02; A61M 11/06; A61M 11/04–042; A61M 11/005; B05B 7/0012;
(Continued)

(56) References Cited

U.S. PATENT DOCUMENTS 4,805,609 A 2/1989 Roberts et al.
5,237,987 A * 8/1993 Anderson ........... A61M 16/024 128/204.18
(Continued)

FOREIGN PATENT DOCUMENTS

WO WO 2009/042187 A1 4/2009
WO WO 2013/165263 A1 11/2013

OTHER PUBLICATIONS

International Search Report and Written Opinion in corresponding International Application No. PCT/EP2015/062972 dated Aug. 7, 2015 (10 pages).

*Primary Examiner* — Cody J Lieuwen
(74) *Attorney, Agent, or Firm* — Bookoff McAndrews, PLLC

(57) ABSTRACT

An aerosol delivery system has a nebulizer and a humidifier providing a gas flow to the nebulizer. A controller varies humidity level of the gas flow to the nebulizer so that if the nebulizer is not operating it has about 100% humidity and it is operating the value is less to allow for the humidification effect of the nebulizer. The control may be achieved by dynamically varying proportions of flow through a dry branch and a humidification branch.

18 Claims, 2 Drawing Sheets

Figure 1:
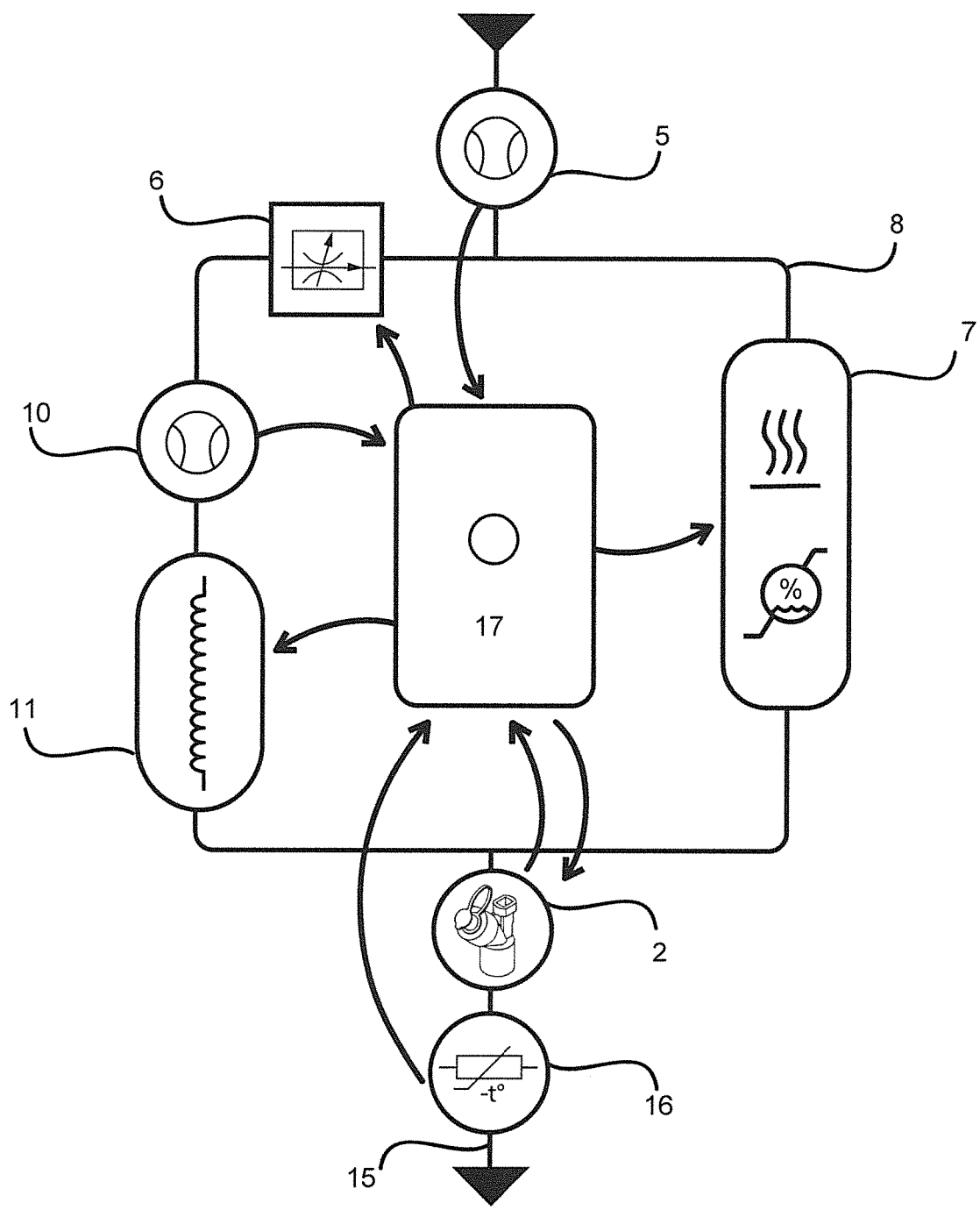

(51) Int. Cl.
*A61M 11/06* (2006.01)
*A61M 16/16* (2006.01)
*A61M 16/00* (2006.01)

(52) U.S. Cl.
CPC .......... *A61M 16/024* (2017.08); *A61M 16/16* (2013.01); *A61M 16/161* (2014.02)

(58) Field of Classification Search
CPC ........ B05B 7/1686; B05B 12/004–008; B05B 12/085; B05B 12/10; B05B 12/12; B05B 17/06; B05B 17/0607; B05B 17/0692
USPC ......................................................... 239/338
See application file for complete search history.

(56) References Cited

U.S. PATENT DOCUMENTS

| | | | | |
|---|---|---|---|---|
| 5,388,571 | A * | 2/1995 | Roberts | A61M 16/16 128/200.18 |
| 7,146,979 | B2 * | 12/2006 | Seakins | A61M 16/0003 128/203.17 |
| 7,934,498 | B1 * | 5/2011 | Heidelberger | A61M 16/20 128/204.17 |
| 2005/0229928 | A1 | 10/2005 | Ivri et al. | |
| 2005/0247305 | A1 * | 11/2005 | Zierenberg | A61M 15/008 128/200.14 |
| 2007/0137646 | A1 * | 6/2007 | Weinstein | A62B 9/003 128/204.17 |
| 2008/0000470 | A1 * | 1/2008 | Minocchieri | A61M 11/02 128/200.21 |
| 2012/0125334 | A1 * | 5/2012 | Korneff | A61M 16/109 128/203.26 |
| 2013/0263852 | A1 | 10/2013 | Montgomery | |

* cited by examiner

AEROSOL DELIVERY SYSTEM WITH HUMIDIFICATION

CROSS-REFERENCE TO RELATED APPLICATIONS

This application is a continuation of U.S. application Ser. No. 15/300,513, filed on Sep. 29, 2016, which is a U.S. national phase entry under 35 U.S.C. § 371 of International Application No. PCT/EP2015/062972, filed on Jun. 10, 2015, which claims priority to European Patent Application No. 14171765.2, filed on Jun. 10, 2014.

INTRODUCTION

The invention relates to aerosol delivery systems (or "nebulizers") with humidification.

WO2013/165263 describes a respiratory humidifier in which a flow generator communicates with a humidifier, and a user interface on the humidifier displays data from a nebulizer of a pulse oximeter.

WO2009/042187 (Nektar Therapeutics) describes a system to introduce aerosolized medicament to a patient which includes a dehumidifier coupled to an inspiratory limb of a ventilator circuit.

An object of the invention is to achieve improved efficiency and reliability in drug delivery.

SUMMARY OF THE INVENTION

According to the invention, there is provided an aerosol delivery system comprising a nebulizer and a humidifier for a nebulizer gas flow, wherein the system comprises a controller configured to vary humidity level of the nebulizer gas flow.

In one embodiment, the controller is configured to reduce the humidity level of gas fed to the nebulizer during nebulizer active time. In one embodiment, the system comprises a sensor for detecting when the nebulizer is active applying medication to the gas flow, and the controller is configured to reduce humidity level of the gas flow to the nebulizer during said active time. In one embodiment the sensor comprises a vision system monitoring plume at the nebulizer.

In one embodiment, the controller is configured to assess the rate at which a nebulizer reservoir liquid volume decreases to calculate the nebulizer output rate.

In one embodiment, the controller is configured to control humidity of the nebulizer gas flow so that the nebulizer brings the relative humidity up to a target level such as about 100% provided to a patient. In one embodiment, the controller is configured to vary humidification according to nebulization rate. In one embodiment, the controller is configured to vary humidification according to gas flow rate.

In one embodiment, the humidifier has a variable output. In one embodiment, the humidifier has a water conduit and a controller for varying water flow rate.

In one embodiment, the system comprises a humidification branch and a dry supply branch linked to the nebulizer, and a flow controller for varying proportions in the branches. In one embodiment, the controller is configured to determine when the nebulizer is active applying medication to the gas flow, and to reduce humidity level during said active time by varying proportions in the branches.

In one embodiment, the system further comprises a temperature sensor to sense temperature of gas flow downstream of the nebulizer, and the controller is configured to use said sensed temperature as an input to vary said humidity level.

In one embodiment, the controller is configured to adjust temperature of gas reaching the nebulizer such that nebulizer output flow has a target temperature.

In one embodiment, the system further comprises a humidity sensor to sense humidity of gas flow downstream of the nebulizer, and the controller is configured to use said sensed humidity as an input to vary said gas flow humidity level.

In one embodiment, the controller is configured to vary nebulizer output rate to vary humidity of nebulizer output flow.

In another aspect, the invention provides a method of controlling an aerosol delivery system having a nebulizer and a humidifier for a nebulizer gas flow, the method comprising varying humidity level of the nebulizer gas flow.

In one embodiment, the method comprises the steps of determining when the nebulizer is active applying medication to the gas flow, and reducing humidity level of the gas flow to the nebulizer during said active time. In one embodiment, the humidity is controlled so that the nebulizer brings the humidity up to a target level provided to a patient. In one embodiment, said target level is about 100%

In one embodiment, the method comprises varying humidification according to nebulization rate.

In one embodiment, the method comprises varying humidification according to gas flow rate.

In one embodiment, a humidifier with a variable output is controlled.

In one embodiment, the system comprises a humidification branch and a dry supply branch, both of said branches linked to the nebulizer, and the controller varies proportions of flow in the branches.

In one embodiment, the controller determines when the nebulizer is active applying medication to the gas flow, and reduces humidity level during said active time, by varying proportions in the branches.

In one embodiment, the system further comprises a temperature sensor to sense temperature of flow downstream of the nebulizer, and the controller uses said sensed temperature as an input to vary said humidity level.

In one embodiment, the controller adjusts temperature of gas reaching the nebulizer such that nebulizer output gas has a target temperature.

In one embodiment, the system further comprises a humidity sensor to sense temperature of flow downstream of the nebulizer, and the controller uses said sensed humidity as an input to vary said gas flow humidity level.

According to the invention there is provided an aerosol delivery system comprising a nebulizer and a humidifier feeding the nebulizer, wherein the system comprises a controller for varying humidity level of gas fed to the nebulizer.

In one embodiment, the system comprises a sensor for detecting when the nebulizer is active applying medication to the gas flow, and the controller is configured to reduce humidity level during said active time.

In one embodiment, the humidity is controlled so that the nebulizer brings the relative humidity up to a target level such as about 100% provided to a patient.

In one embodiment, the controller is configured to vary humidification according to nebulization rate. In one embodiment, the controller is configured to vary humidification according to gas flow rate.

In one embodiment, the humidifier has a variable output. Preferably, the humidifier has a water conduit and a controller for varying water flow rate.

In one embodiment, the system comprises a humidification branch and a dry supply branch feeding the nebulizer, and a flow controller for varying proportions in the branches.

In another aspect, the invention provides a method of controlling an aerosol delivery system having a nebulizer, the method comprising varying humidity level of gas fed to the nebulizer.

In one embodiment, the method comprises detecting when the nebulizer is active applying medication to the gas flow, and reducing humidity level during said active time.

In one embodiment, the humidity is controlled so that the nebulizer brings the relative humidity up to a target level such as about 100% provided to a patient.

In one embodiment, the method comprises varying humidification according to nebulization rate. In one embodiment, the method comprises varying humidification according to gas flow rate.

In one embodiment, a humidifier with a variable output is controlled.

In one embodiment, the system comprises a humidification branch and a dry supply branch feeding the nebulizer, and the method varies proportions of flow in the branches.

DETAILED DESCRIPTION OF THE INVENTION

Figure 2:
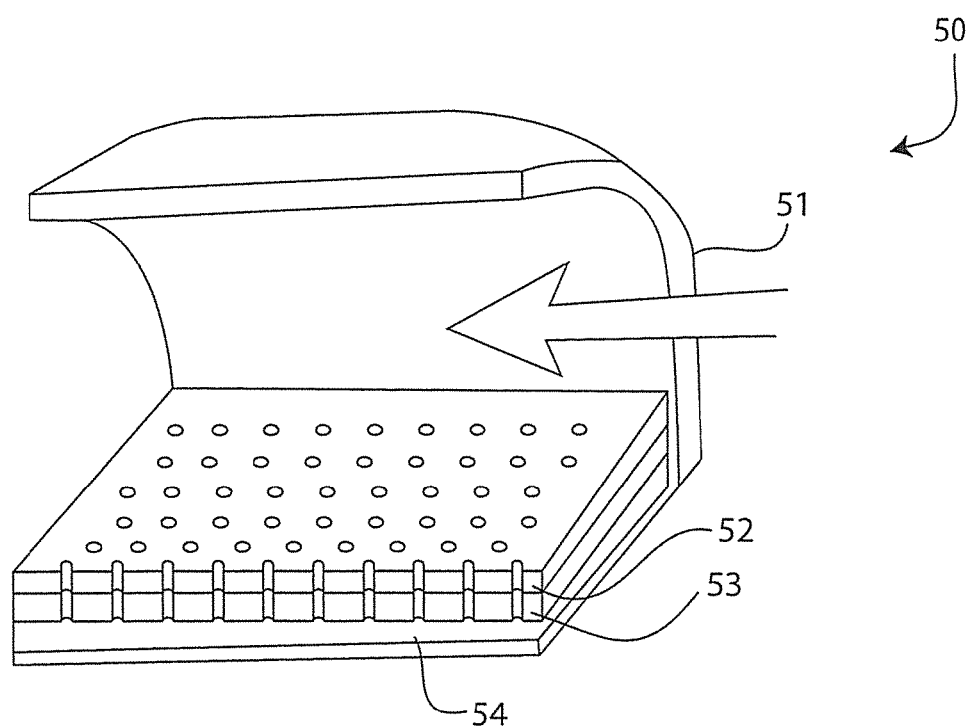

The invention will be more clearly understood from the following description of some embodiments thereof, given by way of example only with reference to the accompanying drawings in which:

FIG. 1 is a block diagram illustrating an aerosol delivery system of the invention, in which two branches feed a nebulizer; and FIG. 2 is a partly cut-away perspective view showing a humidifier of an alternative system, the humidifier having a variable humidity output.

Referring to FIG. 1 an aerosol delivery system 1 comprises a nebulizer 2. Gas is supplied to the nebulizer 2 via an inlet 5 incorporating a gas pressure sensor operating up to about 80 cmH$_2$O. An alternative to this component is a flow sensor, which would operate up to about 150 l/min.

The flow from the inlet 5 is divided into two branches as follows:

(a) A valve/flow restrictor 6 to govern flow towards a pressure sensor 10 feeding a heater 11. The valve 6 restricts flow so that it dictates what percentage of flow entering the system via the inlet 5 is directed down each limb. The sensor 10 is optional, in this embodiment, serving as a check that the valve is allowing the right amount of gas to flow through. The valve 6 component may in other embodiments be a variable flow restrictor. The components 6 and 10 could be on either limb. They are included to ensure that the correct ratio of the incoming gas flow goes down each limb, and as such could work as well on either or both limbs.

It may also be beneficial to have a valve/flow restrictor immediately after the valve 5 to remove the need for the user (e.g. clinician) to use an external gas flow regulator.

(b) A humidifier 7 incorporating a heater linked to the inlet 5 by a biocompatible tube 8. The components may or may not be connected by tubing, for example they may be connected directly to each other, and where there is a tube it may not be biocompatible.

The branches, namely the outlets of the heater 11 and of the humidifier 7, are joined at the nebulizer 2 inlet.

The nebulizer 2 aerosolizes a liquid (water, saline, therapeutics, etc.) into the gas flow and via a temperature and/or humidity sensor 16 through an outlet line 15 to a patient interface.

The inlet 5 is in one embodiment a digital, in-line, fast update, self-calibrating sensor such as the Sensirion SFM3000™ (http://www.sensirion.com/en/products/mass-flow-meters-for-gases/mass-flow-meter-sfm3000/) or similar. However, any flow sensor capable of detecting flows of 0-150 lpm+/−10% or pressure sensor capable of detecting accurately 80 cmH$_2$O would suffice. These sensors will establish flow through either infrared, thermal senor, chemical, mechanical or pressure means.

The valve/flow restrictor 6 is in one embodiment an electronically modulating flow control gas valve, to provide the required accuracy required for this system. A single valve may not be optimum to cover the entire range of flows required for this application, and so it may require two. For example a Proportionair FQB3™ control valve would cover flows greater than 28 lpm and the FQPV™ control valve for lower flow rates. Both these valves can be provided with a Proportionair F-Series™ flow sensor so that component would provide the functionality of the component 10.

The inlet 5 could also comprise such a valve/sensor pair.

The humidifier 7 comprises a water reservoir and a means of heating. This can be as simple as a liquid feed onto a hotplate, or a more complex arrangement such as the humidifier 50 described below.

The heater 11 is of the known type having a helical coil heating element to maximise surface area exposed to the gas flow. Alternatively, the heater could be of the type having a heated metallic or ceramic cylinder through which the gas flows.

There is a controller, 17, linked to the illustrated system components. This dynamically controls the valve 6 to govern the proportions of gas flow in the two branches. The inlet 5 measures the gas flow into the system.

It is known that adequate humidification of ventilator patient circuits is essential to maintaining mucociliary clearance levels within the patient airways. As humidity levels decrease below optimal (44 mg/l) cilia activity reduces causing slower mucociliary clearance leading to secretion drying and accumulation. This manifests as patient discomfort, coughing, reduced lung function and potentially airway occlusion. High relative humidity levels reduce the carrying capacity of the gas resulting in less bacteria and viruses being transported into the airways.

As air passes through a standard humidified circuit temperature fluctuations and/or aerosol is added and this results in a humidity drop (absolute and/or relative) and/or precipitation of water vapour and/or aerosol within the circuit. These issues can cause circuit occlusions, interfere with ventilation settings and/or cause patient discomfort through nasal prongs splutter.

By controlling humidity levels such that the gas isn't saturated when it reaches the nebuliser the apparatus can increase the amount of drug reaching the patient by reducing precipitation of water vapour and/or aerosol within the circuit This mechanism has the additional benefit of resulting in less precipitation being blown towards the patient causing discomfort, for example when there are large droplets exiting the nasal prongs.

The control algorithm executed by the controller 17 sets how much flow should go through each limb, and the valve/flow restrictor 6 adjusts to achieve these values. Furthermore, the controller monitors temperature and humidity as detected by the temperature and humidity sensor (16) and adjusts the temperature of the heater and/or humidifier such that the air reaching the patient achieves the user inputted/default temperature and humidity. The reason for positioning this sensor after the nebuliser is that as the nebuliser adds moisture it also has a slight cooling effect—in practice this means that the air reaching the nebuliser will have to be heated to slightly above the target temperature.

If there is 100% flow through the humidifier 7 the flow into the nebulizer 2 will have close to 100% relative humidity. This is acceptable, and indeed desirable, while the nebulizer is passively allowing flow without medication. However, when medication is being added by the nebulizer 2 the nebulizer input humidity is preferably less than 100%, say 68%. The nebulizer 2 then brings the humidity level up to 100% by aerosolizing the liquid medication. Hence an optimum balance of medication aerosolization and humidity is achieved. Humidifiers may achieve close to 100% relative humidity at low gas flow rates but in practice the higher the gas flow rate the further the air is from saturated.

The components of the system have digital outputs and inputs and the controller implements the following control scheme:
  Nebuliser Output (ml/min)/Target Humidity Level (ml/l) =Gas Flow Rate through Heat only Limb (l/min)
  Target Gas Flow Rate (ml/min)/Gas Flow Rate through Heat only Limb (l/min)=Gas Flow Rate through Heated+Humified Limb (l/min)

The flow/pressure sensor 5 measures the gas flow entering the circuit. It then transmits this information to the controller 17. The gas flow entering the system is set typically on an external gas flow regulator, however, for greater control and convenience another flow restrictor/valve could be incorporated immediately after the sensor 5. The controller 17 then performs a calculation based on the information received from the sensor 5 as to how much gas should be directed through each limb. Target temperature and/or humidity are factored into this calculation and may be clinician set or pre-programmed.

In order to calculate the temperature and humidity levels required to achieve target temperature and humidity levels post aerosol inclusion the controller 17 authenticates that a nebulizer is connected and that it is actively aerosolizing. It also authenticates the nebulizer output rate to calculate the required flow split down each limb. This authentication may be achieved by:
  Plume detection, such as by a vision system with a camera which monitors the extent of plume in the immediate vicinity of the nebulizer. Such monitoring may for example use image processing techniques to monitor the overall plume size in a two-dimensional plane.
  Continuous or intermittent measurement of the volume of medication remaining in the nebulizer reservoir. By assessing the rate at which the reservoir liquid volume decreases the controller calculates the nebulizer output rate.
  The controller being programmed to assume a set value (e.g. 0.4 ml/min) that is representative of the average and expected nebulizer output rate.
  Receiving a signal from a nebulizer with a capability to provide activation and operating level data.

Based on the nebulizer output rate information received the controller then calculates how much of the initial gas flow to split down each limb. This flow splitting is achieved by controlling the flow restrictor/valve 6. The sensor 16 also transmits information to the controller enabling it to set the humidifier and heater to appropriate temperatures.

In a summary of the electronic components interaction; all of the sensors send information to the controller, the controller authenticates this information and based on calculations it performs it transmits commands to the valves/flow restrictors and the humidifier and the heater components of the system to adjust to specific settings. The nebulizer and controller exchange information—the nebulizer transmits information indicating when it is nebulising and in some embodiments output rate. The controller sends the drive signal to the nebulizer.

It is envisaged that the controller could modify this drive signal to increase or decrease the nebulizer output rate if this was a preferred way of achieving 100% humidity for example if the drug is not required to be delivered fast. The algorithm accommodates this potential variable.

Target gas flow rate, target humidity and target temperature can be user inputs or can be pre-programmed to default values. Humidity and temperature reaching the patient will be verified by the sensor (16) post nebulizer and pre-patient.

In the table below (Table 1) there is a fixed nebulizer output, however in other control schemes it could also be measured or controlled. There are two target humidity values indicative of current understanding of the area, 44 mg/l (0.044 ml/l) which is typically considered optimal humidity and 32 mg/l (0.032 ml/l) which is often considered essential humidity. Optimal humidity is at 3TC and essential humidity is at 31° C.

To take the example of a target gas flow rate to the patient of 40 l/min at optimal humidity levels (44 mg/l) for a nebulizer with an output rate of 0.4 ml/min. In this case 9.09 l/min would be directed down the heated only limb while 30.91 l/min would be directed down the heated and humidified limb. However, these proportions do not stay constant with increasing output (target gas flow). For example, at an overall system output of 100 l/min at optimal humidity levels (44 mg/l) for a nebulizer with an output rate of 0.4 ml/min 9.09 l/min would still be directed down the heated only limb but now 90.91 l/min will be directed down the humidifier limb.

TABLE 1

Example of gas flow rate spit by limb for a specified nebuliser output rate for varying gas flow rates across two different target humidity levels.

| Target Humidity Level (ml/l) | Nebuliser Output (ml/min) | Target Gas Flow Rate (l/min) | Heat Only Limb Gas Flow Rate (l/min) | Heated + Humidified Limb Gas Flow Rate (l/min) |
|---|---|---|---|---|
| 0.032 | 0.4 | 10  | 10.00 | 0.00  |
| 0.044 | 0.4 | 10  | 9.09  | 0.91  |
| 0.032 | 0.4 | 20  | 12.50 | 7.50  |
| 0.044 | 0.4 | 20  | 9.09  | 10.91 |
| 0.032 | 0.4 | 40  | 12.50 | 27.50 |
| 0.044 | 0.4 | 40  | 9.09  | 30.91 |
| 0.032 | 0.4 | 80  | 12.50 | 67.50 |
| 0.044 | 0.4 | 80  | 9.09  | 70.91 |
| 0.032 | 0.4 | 100 | 12.50 | 87.50 |
| 0.044 | 0.4 | 100 | 9.09  | 90.91 |

In an embodiment with integrated components the controller will authenticate from the flow/pressure sensor 5 how much flow is entering the system and the flow from the nebuliser 2 if aerosol is being produced and if so at what rate. It will then calculate what percentage humidity is required (for the selected gas flow rate) to reach the nebuliser such that when combined with nebuliser aerosol output the gas reaching the patient is optimal (44 mg/l @ 37° C.) or achieving the user specified levels and at the clinician-inputted (or automatic) temperature. This essentially determines what proportion of gas entering the system must pass through the heater 11 and what proportion must pass through the humidifier 7. Based on this information the flow will be restricted by the valve 6 to ensure this split. When the dose is delivered 100% of flow will pass through the humidifier 7.

The following are the approximate parameter values for one exemplary embodiment:
  Optimal humidity: 44 mg/l @ 37° C. (0.044 ml/l assuming water vapour)
  Gas flow rate entering system: 30 l/min
  Nebuliser output rate: 0.4 ml/min The nebuliser can bring ~10 l/min up to optimal humidity levels. Therefore, for the entire 30 l/min to reach optimal humidity levels 20 l/min must pass through the heated and humidified limb 7 and 10 l/min through the heater-only limb.

It will be appreciated that by having a "dry" branch and a humidifier branch there can be continuously an optimum split between the two for optimum gas flow to the patient.

Referring to FIG. 2 an alternative approach is illustrated, with only one supply to the nebuliser. A humidifier 50 has a housing 51 for air flow and it incorporates:
  a heater 52,
  an insulating layer 53, and
  a water layer 54.

This arrangement allows humidity level to be controlled by controlling supply of water to be vaporised/evaporated. The porous heater plate controls temperature and the rate at which water is pumped up to it/made available to it controls humidity.

The humidifier has a controller, not shown, which dynamically varies water flow rate and heater operating parameters in order to control the level of humidification and temperature. This achieves, in a single flow to the nebuliser input, the level of control achieved by the two branches of the system 1.

It will be appreciated that the invention overcomes the existing problem of air passing through a standard humidified circuit being ~100% humidified, thus decreasing the aerosol carrying capacity of the air—increasing precipitation within the circuit, with resultant decrease in efficiency of therapeutic aerosol delivery. It can create an aerosol "window" in which the humidity of the air reaching the nebulizer is decreased to a level less than 100% so that when aerosol is added the air is 100% humidified. This should serve to decrease aerosol losses due to precipitation from insufficient gas carrying capacity. When humidification levels are stepped down heating of standard circuit heating wires would be increased.

The humidity level reaching the nebuliser is controlled by either limiting liquid availability (FIG. 2) or through the ratio of gas directed through a heated and humidified limb versus a humidified only limb (FIG. 1). The optimal level of humidity reaching the nebuliser is calculated based on gas flow rate, clinician inputs (desired temperature and desired humidity level), and potentially nebuliser output rate. Nebuliser output rate may be assumed to be constant, actively measured, or communicated by clinician or integrated tag.

A benefit is that humidity levels are maintained and that droplet size is decreased due to heating in a reduced humidity environment. Smaller droplets are more likely to reach the patient.

It is our understanding that heating tends to reduce the droplet size, thereby improving the delivery efficiency, particularly for low humidity. Also, by dynamically keeping the humidity at or just below 100% the level of precipitation is reduced.

The invention is not limited to the embodiments described but may be varied in construction and detail. For example, it is not essential that the nebulizer bring the relative humidity up to about 100%, it may be a different value which is desired for optimum therapy. The term "medication" covers any substance added to the nebulizer gas flow, including any liquid such as water, saline, or therapeutics.

The invention claimed is:

1. A method of controlling an aerosol delivery system, comprising:
  determining when a nebulizer is actively delivering medication; and
  when the nebulizer is actively delivering medication, dynamically varying a humidity level of a gas flow upstream of the nebulizer via a humidifier in communication with a controller to achieve a target humidity level of the gas flow upstream of the nebulizer, and
  wherein the varying of the humidity level includes, as often as necessary, adjusting a gas flow valve positioned upstream of a humidification branch of a gas flow circuit, the humidification branch including the humidifier, and the gas flow valve being further positioned upstream of the nebulizer
  wherein a required variation in humidity is continuously determined by the controller;
  wherein the determination of the required variation of humidity is based on a humidity downstream of the nebulizer;
  wherein the humidity downstream of the nebulizer is measured by a humidity sensor located downstream of the nebulizer; and
  wherein the varying of the humidity level occurs when the nebulizer is actively delivering medication.

2. The method of claim 1, wherein, if the nebulizer is actively delivering medication, the controller transmits a signal to the gas flow valve to reduce a proportion of the gas flow passing through the humidification branch upstream of the nebulizer.

3. The method of claim 1, wherein, if the nebulizer is not actively delivering medication, the controller transmits a signal to the gas flow valve such that an entirety of the gas flow upstream of the nebulizer passes through the humidification branch upstream of the nebulizer.

4. The method of claim 1, wherein the varying of the humidity level includes adjusting the gas flow valve external and upstream of the nebulizer to achieve the target humidity level of about 100%.

5. The method of claim 1, further including sensing a temperature of the gas flow downstream of the nebulizer via a temperature sensor in communication with the controller, and wherein the varying of the humidity level of the gas flow is based on, at least in part, the sensed temperature.

6. The method of claim 1, wherein the varying of the humidity level of the gas flow is based on, at least in part, a gas flow rate.

7. The method of claim 1, wherein the determining when the nebulizer is actively delivering medication includes sensing, by a sensor, when the nebulizer is actively delivering medication.

8. The method of claim 7, wherein the sensor includes a vision system, and the method further includes monitoring, by the vision system, plume at the nebulizer.

9. The method of claim 1, further including varying an output rate of the nebulizer to vary a humidity level of gas flow at an exit of the nebulizer.

10. A method of controlling an aerosol delivery system, comprising:
sensing a humidity level of a gas flow at an exit of a nebulizer of a gas flow circuit; and
based on the sensing, adjusting a proportion of the gas flow entering a humidification branch of the gas flow circuit upstream of the nebulizer to vary a humidity level of the gas flow to the nebulizer such that the humidity level of the gas flow at the exit of the nebulizer is maintained at about 100% when (1) the nebulizer is actively delivering aerosol to the gas flow circuit, and (2) when the nebulizer is not delivering aerosol to the gas flow circuit;
wherein actively varying a humidity level comprises continuing to vary the humidity level of the gas by continually sensing a humidity level of the gas flow at the exit of the nebulizer; and
wherein a required variation in humidity level is determined by a controller based at least in part on sensing of the humidity level of the gas flow at the exit of the nebulizer.

11. The method of claim 10, wherein adjusting the proportion of the gas flow entering the humidification branch of the gas flow circuit is based on, at least in part, a gas flow rate.

12. The method of claim 10, wherein, if the nebulizer is not actively delivering aerosol to the gas flow circuit, an entirety of the gas flow upstream of the nebulizer passes through the humidification branch of the gas flow circuit.

13. The method of claim 10, wherein the gas flow circuit includes a gas inlet line, the humidification branch, a dry supply branch, and a nebulization line, wherein each of the humidification branch and the dry supply branch have an upstream end in fluid communication with a downstream end of the inlet line, and wherein each of the humidification branch and the dry supply branch have a downstream end in fluid communication with an upstream end of the nebulization line.

14. A method of controlling an aerosol delivery system, comprising:
determining when a nebulizer is actively delivering medication; and
varying a humidity level of a gas flow upstream of the nebulizer via a humidifier in communication with a controller to achieve a target humidity level of the gas flow upstream of the nebulizer,
wherein the varying of the humidity level includes adjusting a gas flow valve positioned upstream of a humidification branch of a gas flow circuit, the humidification branch including the humidifier, and the gas flow valve being further positioned upstream of the nebulizer,
wherein when the nebulizer is actively delivering medication, the varying the humidity level includes controlling the gas flow valve to reduce a proportion of the gas flow passing through the humidification branch, and
wherein when the nebulizer is not actively delivering medication, the varying the humidity level includes controlling the gas flow valve such that an entirety of the gas flow upstream of the nebulizer passes through the humidification branch upstream of the nebulizer;
wherein a required variation in humidification is continuously determined by the controller;
wherein the determination of the required variation of humidification is based on a humidity downstream of the nebulizer;
wherein the humidity downstream of the nebulizer is measured by a humidity sensor located downstream of the nebulizer; and
wherein varying of the humidity level is performed as often as necessary based on the determined required variation in humidification.

15. The method of claim 14, wherein the varying of the humidity level includes adjusting the gas flow valve external and upstream of the nebulizer to achieve the target humidity level of about 100%.

16. The method of claim 14, further including sensing a temperature of the gas flow downstream of the nebulizer via a temperature sensor in communication with the controller, and wherein the varying of the humidity level of the gas flow is based on, at least in part, the sensed temperature.

17. The method of claim 14, wherein the varying of the humidity level of the gas flow is based on, at least in part, a gas flow rate.

18. The method of claim 14, wherein the determining when the nebulizer is actively delivering medication includes sensing, by a sensor, when the nebulizer is actively delivering medication.

* * * * *